(12) United States Patent
Gaudet et al.

(10) Patent No.: US 9,551,690 B2
(45) Date of Patent: Jan. 24, 2017

(54) PROFILING TOOL FOR DETERMINING MATERIAL THICKNESS FOR INSPECTION SITES HAVING COMPLEX TOPOGRAPHY

(75) Inventors: Michel Joseph Gilles Gaudet, Pembroke (CA); Robert Hayden Lumsden, Petawawa (CA); Glenn Curtis Longhurst, Deep River (CA); Kristopher Kyle Jones, Deep River (CA); Stuart Thomas Craig, Deep River (CA); David Walter Dunford, Deep River (CA); Paul Gregory Adams, Deep River (CA); Kenneth Robert Chaplin, Deep River (CA); Helene Marie Hebert, Deep River (CA)

(73) Assignee: Atomic Energy Of Canada Limited, Chalk River, ON (CA)

( * ) Notice: Subject to any disclaimer, the term of this patent is extended or adjusted under 35 U.S.C. 154(b) by 429 days.

(21) Appl. No.: 14/008,739

(22) PCT Filed: Mar. 30, 2012

(86) PCT No.: PCT/CA2012/050205
§ 371 (c)(1),
(2), (4) Date: Sep. 30, 2013

(87) PCT Pub. No.: WO2012/129703
PCT Pub. Date: Oct. 4, 2012

(65) Prior Publication Data
US 2014/0076053 A1    Mar. 20, 2014

Related U.S. Application Data

(60) Provisional application No. 61/470,119, filed on Mar. 31, 2011.

(51) Int. Cl.
*G01N 29/04* (2006.01)
*G01N 29/26* (2006.01)
(Continued)

(52) U.S. Cl.
CPC ............ *G01N 29/04* (2013.01); *G01B 17/02* (2013.01); *G01N 29/225* (2013.01);
(Continued)

(58) Field of Classification Search
CPC .... G01N 29/04; G01N 29/225; G01N 29/262; G01N 29/265; G01N 29/07; G01N 29/28
(Continued)

(56) References Cited

U.S. PATENT DOCUMENTS 3,575,044 A * 4/1971 Gibbs ............... G01N 29/0636
228/104
3,921,440 A 11/1975 Toth
(Continued)

FOREIGN PATENT DOCUMENTS

JP    2006170685    6/2006

OTHER PUBLICATIONS

Extended European Search Reported, Dated Sep. 2, 2014, Application No. 12765562.9.

*Primary Examiner* — Helen Kwok
(74) *Attorney, Agent, or Firm* — Anderson Gorecki & Rouille LLP

(57) ABSTRACT

A phased array ultrasonic probe may be mounted to a component to be inspected for wall thickness on an apparatus that includes a split ring adapted to be magnetically held in place on the component. In particular, the probe may be mounted to a carriage connected to the split ring in a manner that allows the carriage to rotate around the split ring while the probe is in operation. Between the probe and the component, a transducer shoe defining, by a flexible membrane, a cavity and an aperture. Conveniently, the construction of the flexible membrane allows wall thickness measurements to be acquired in portions of the component that have complex topography, such as welds. The apparatus is
(Continued)

installed on an adaptor assembly for inspection of straight section of pipes. This adaptor assembly is not used in absence of straight section. By acquiring data from multiple output pulse transmitted at multiple incidence angles, processing software may conveniently produce an accurate wall thickness map of the area of interest on the component.

5 Claims, 12 Drawing Sheets

(51) Int. Cl.
  *G01B 17/02* (2006.01)
  *G21C 17/017* (2006.01)
  *G01N 29/22* (2006.01)
(52) U.S. Cl.
  CPC ........ *G01N 29/262* (2013.01); *G21C 17/017* (2013.01); *G01N 2291/267* (2013.01)
(58) Field of Classification Search
  USPC ......... 73/588, 622, 623, 632, 633, 638, 643, 73/644, 865.8
  See application file for complete search history.

(56) References Cited

U.S. PATENT DOCUMENTS

| | | | | |
|---|---|---|---|---|
| 4,092,867 | A * | 6/1978 | Matzuk | A61B 8/00 600/445 |
| 4,649,925 | A * | 3/1987 | Dow | G01N 29/265 600/446 |
| 7,841,237 | B2 * | 11/2010 | Suzuki | G01N 29/07 73/584 |
| 8,141,442 | B2 * | 3/2012 | Roberts | F17D 5/00 73/865.8 |
| 2004/0016299 | A1 | 1/2004 | Glascock et al. | |
| 2009/0038398 | A1 | 2/2009 | Lavoie et al. | |
| 2009/0301203 | A1 * | 12/2009 | Brussieux | G01N 29/225 73/627 |
| 2010/0224001 | A1 * | 9/2010 | Brignac | G01N 29/07 73/639 |
| 2010/0236330 | A1 * | 9/2010 | Nyholt | G01N 29/223 73/644 |
| 2010/0275691 | A1 * | 11/2010 | Roberts | G01N 27/90 73/622 |
| 2010/0288049 | A1 * | 11/2010 | Hoyt | G01N 29/043 73/602 |
| 2011/0303013 | A1 * | 12/2011 | Kass | G01N 29/28 73/632 |

* cited by examiner

PROFILING TOOL FOR DETERMINING MATERIAL THICKNESS FOR INSPECTION SITES HAVING COMPLEX TOPOGRAPHY

CROSS-REFERENCE TO RELATED APPLICATION

This application claims the benefit of and priority to U.S. Provisional Patent Application No. 61/470,119 filed Mar. 31, 2011 under the title PROFILING TOOL FOR DETERMINING MATERIAL THICKNESS FOR INSPECTION SITES HAVING COMPLEX TOPOGRAPHY.

The content of the above patent application is hereby expressly incorporated by reference into the detailed description hereof.

FIELD

The present application relates generally to an apparatus for inspecting material thickness and, more specifically, to a profiling tool for determining material thickness for inspection sites having complex topography.

BACKGROUND

In some nuclear reactors, feeder pipes allow heavy water to circulate to each fuel channel. Over the course of the life of the reactor, these feeder pipes may erode and/or corrode internally due to the flow accelerated corrosion under and adjacent to welds. Periodic inspections are required to determine the remaining material thickness at the weld and surrounding area for fitness-for-service assessment.

The outside surface of the inspection site offers a complex topography which includes weld crowns, curved fittings or bends, and tapered surfaces that hinders the collection of wall thickness measurements using conventional ultrasonic tools.

BRIEF DESCRIPTION OF THE DRAWINGS

Reference will now be made, by way of example, to the accompanying drawings which show example implementations; and in which.

DETAILED DESCRIPTION

Figure 1:
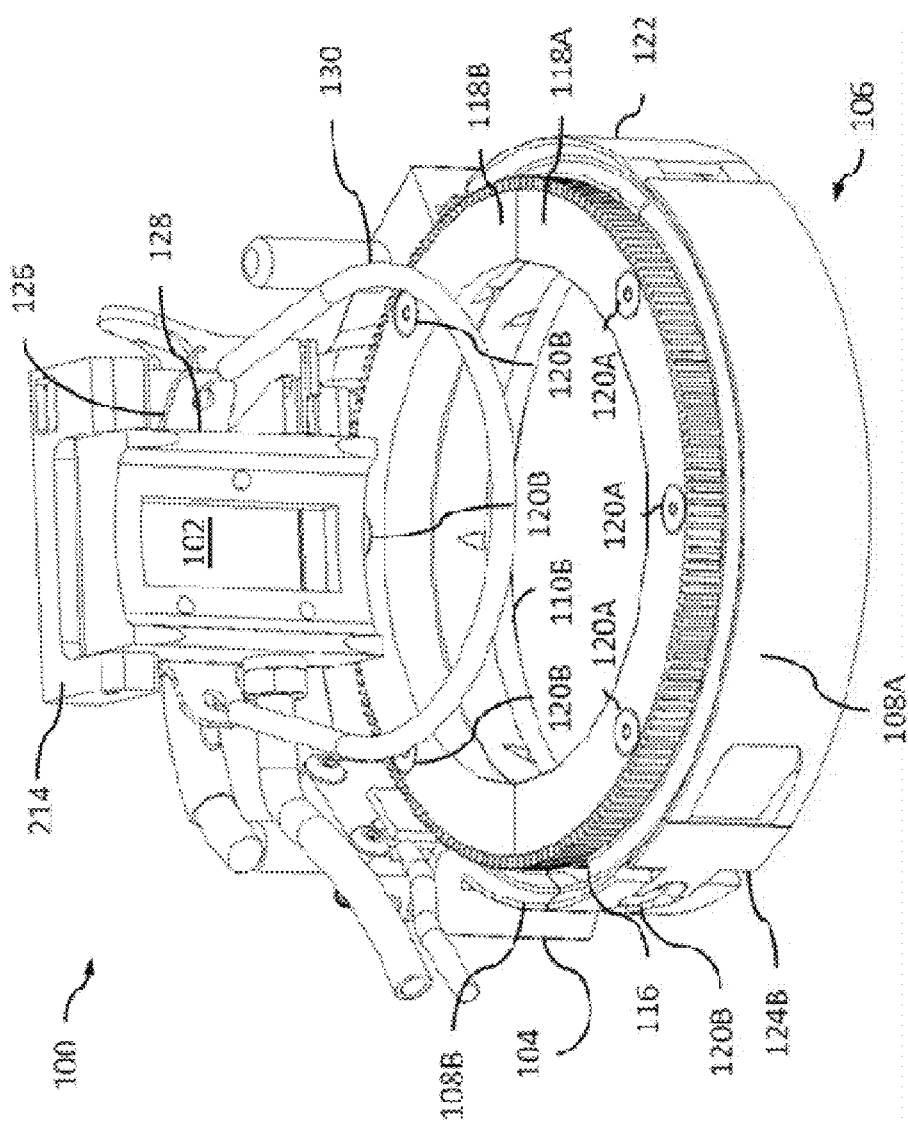
FIG. 1 illustrates a delivery tool assembly according to an embodiment of the present application, the delivery tool assembly including a split ring assembly.

Wall thickness adjacent to welds in feeder pipes is conventionally determined using single point, ultrasonic probes, sometimes with several probes bundled in a pattern using a rigid transducer shoe. In this application, a shoe is a device mounted to an ultrasonic transducer that performs two purposes: it provides the required physical stand-off between the transducer and the object being measured, and; it also provides a medium for the transmission of the ultrasonic signal from the transducer. The ultrasonic signal generated at a single, fixed ultrasound angle by each probe is recorded, the probe or probe bundle is moved a pre-determined distance along the axial or circumferential axis of the feeder, and the signals are recorded again. This is repeated as many times as required or practical to cover the area of interest.

Wall thickness measurements through the weld crowns are limited to selected locations using point-like pencil probes.

A two-dimensional wall thickness map may be created using one ultrasound angle with UltraVision® (a product from Zetec, Inc. of Snoqualmie, Wash.) subtracting the time delay of the signal that crosses two gates. This can be done if the geometry of the component being inspected is relatively flat and if two back-wall echoes are detected.

However, this approach has some drawbacks. For example, the physical requirements of grouping conventional probes of discrete dimensions within a probe assembly can lead to relatively large gaps in the inspection coverage. Such gaps may lead to an inspection missing small localized thinning regions that could be significant for a fitness-for-service assessment. Furthermore, the inspection of curved topography such as feeder pipe bends or weld crowns requires that the probe active surface be normal to the outside surface of the component to obtain data, which is not possible on highly curved feeders and weld crowns when using a conventional probe that can only transmit and receive a signal along a discrete ultrasound angle. Still further, a homogeneous couplant between the transducer face and surface to be inspected may be required to obtain an acceptable signal. The current inspection tools use a solid transducer shoe that cannot follow the local features such as weld crowns and highly curved feeder bends, leading to a loss of couplant and data. Abrupt changes in the profile of the surface to be inspected such as welds are a special challenge. Due to the physical size of the probe and solid transducer shoe, no data can be obtained in a zone equal to one half the diameter of the probe from the profile change. Weld areas are susceptible to have flow accelerated corrosion, with no inspection tool available with the current technology for areas immediately adjacent to a weld. Locating a probe to a repeatable location remains a challenge. Conventional tools that inspect feeder pipes adjacent to welds do not record a reference position intrinsic to the data, leading to positional uncertainties.

The present application is related to a delivery tool that includes a phased array ultrasonic probe assembly, mounted on a rotating carriage that permits acquisition of a plurality of closely spaced data points using multiple incidence angles simultaneously and saving these data points for subsequent analysis. The probe is mounted in a transducer shoe in which a couplant-filled cavity is defined by a flexible membrane seal capable of conforming to a complex topography. The transducer shoe is connected to the carriage via an adjustable pivoting arm, which is mounted on a split ring that is magnetically held in place around the feeder component to be inspected (e.g., Grayloc hub or feeder pipe) as the tool is operated. An encoder provides angular position feedback.

According to an aspect of the present disclosure, there is provided an apparatus for inspecting a component. The apparatus includes a magnetized split ring to maintain a position on the component, a carriage mounted on the split ring in a manner allowing the carriage to rotate around the split ring, a transducer shoe, connected to the carriage by the pivoting arm, with the transducer shoe maintaining by a flexible membrane a cavity for receiving a couplant, the flexible membrane also defining an aperture, a phased array ultrasonic probe, mounted to the transducer shoe and an encoder adapted to provide angular position information.

According to a further aspect of the present disclosure, there is provided a method of creating a wall thickness image from data acquired using a phased array ultrasonic probe, the data relating a voltage measurement to a time, an ultrasonic angle, an axial position and a circumferential position. The method includes, for a given ultrasonic angle, selecting an axial position, thereby providing a selected axial position, selecting a circumferential position, thereby providing a selected circumferential position, determining a wall thickness value and associating the wall thickness value with the axial position and the circumferential position. The method also includes repeating the selecting of a circumferential position, determining and associating for a plurality of circumferential positions, repeating the repeating for a plurality of axial positions and producing a map of wall thickness for the plurality of circumferential positions and the plurality of axial positions. In other aspects of the present application, a processor is provided, adapted for carrying out this method and a computer readable medium is provided for adapting a processor in a general purpose computer to carry out this method.

Other aspects and features of the present disclosure will become apparent to those of ordinary skill in the art upon review of the following description of specific implementations of the disclosure in conjunction with the accompanying figures.

FIG. 1 illustrates a delivery tool assembly 100 that includes a phased array ultrasonic probe 102 mounted on a carriage 104 that is arranged to rotate on a split ring 106 sized to fit around a component to be inspected (not shown).

Figure 3:
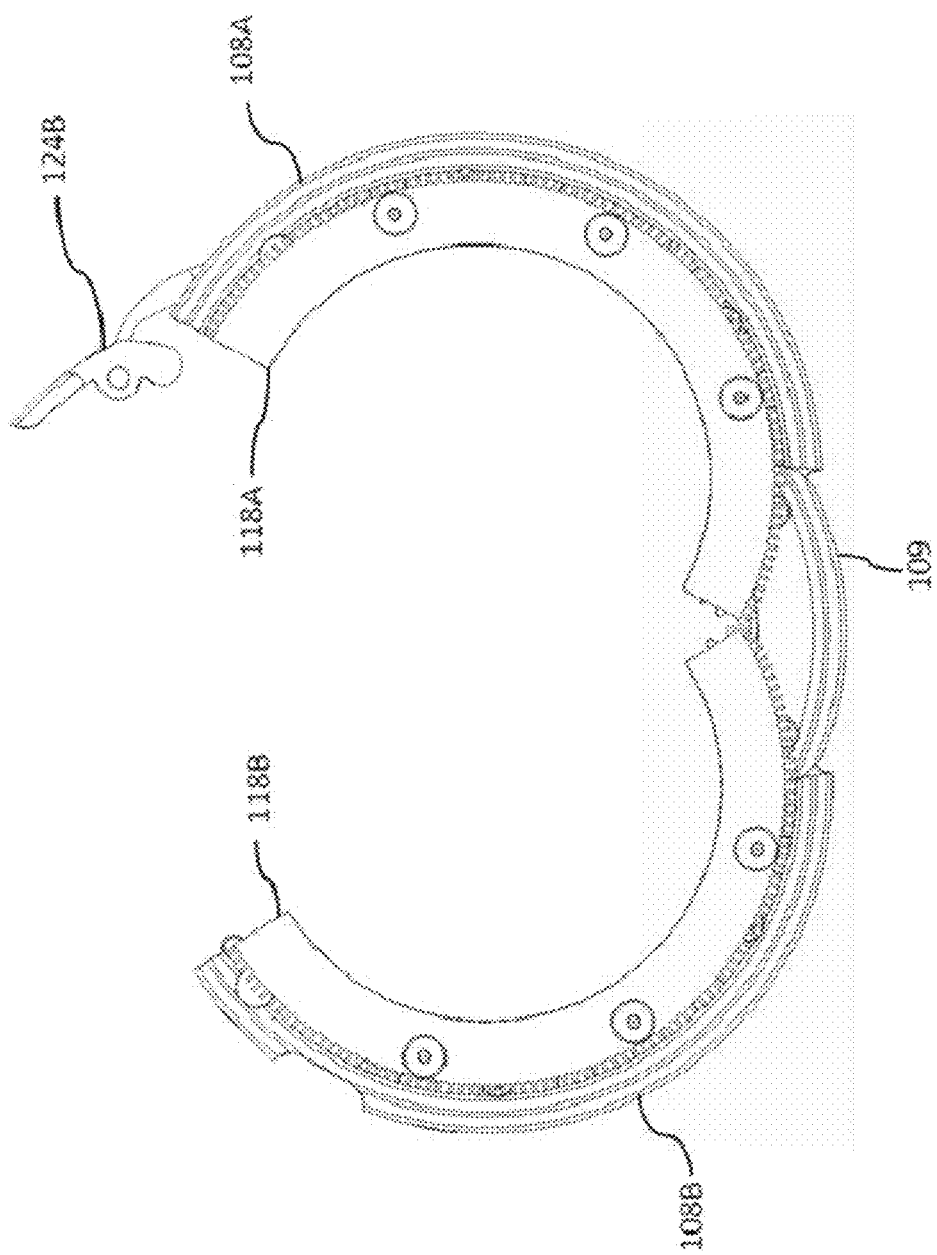
FIG. 3 illustrates, in plan view, the split ring assembly of the delivery tool assembly of FIG. 1, with the split ring assembly in an open position.
Figure 4:
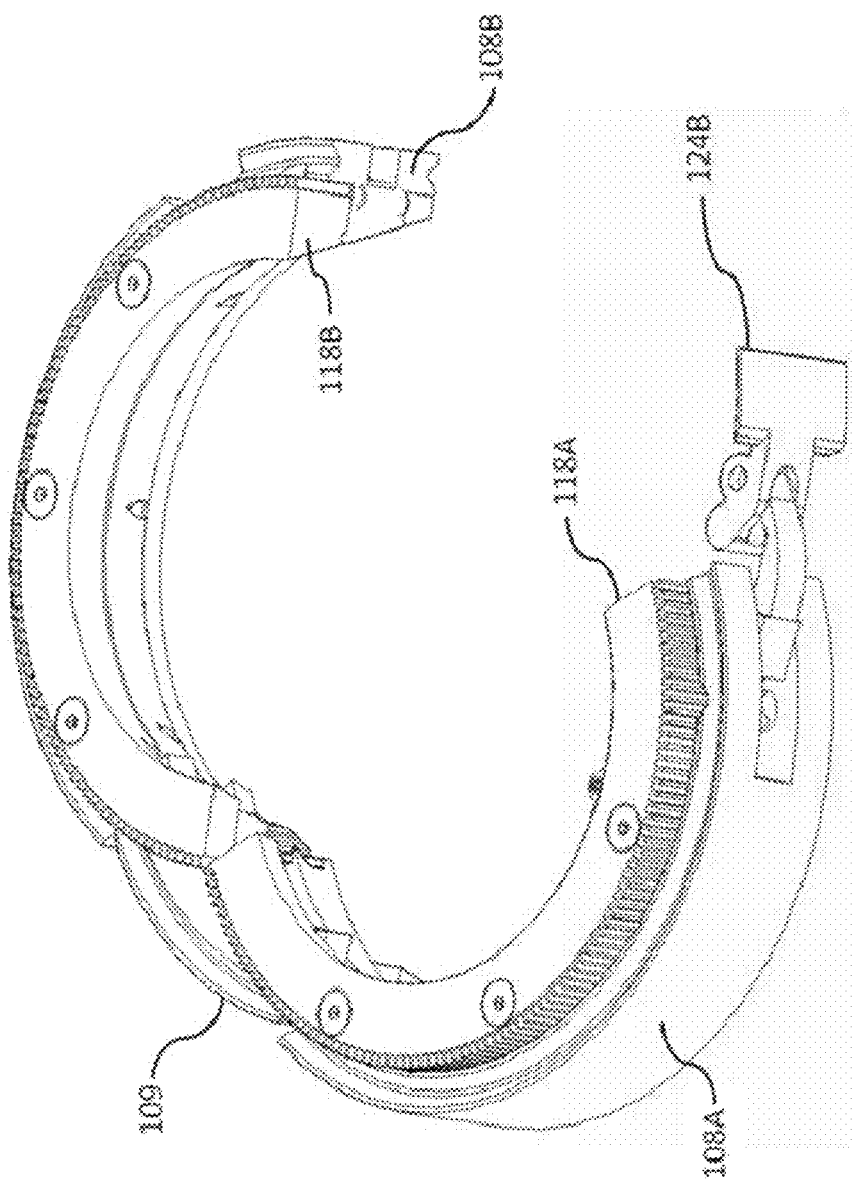
FIG. 4 illustrates, in an isometric view, the split ring assembly of FIG. 3 in the open position.
Figure 5:
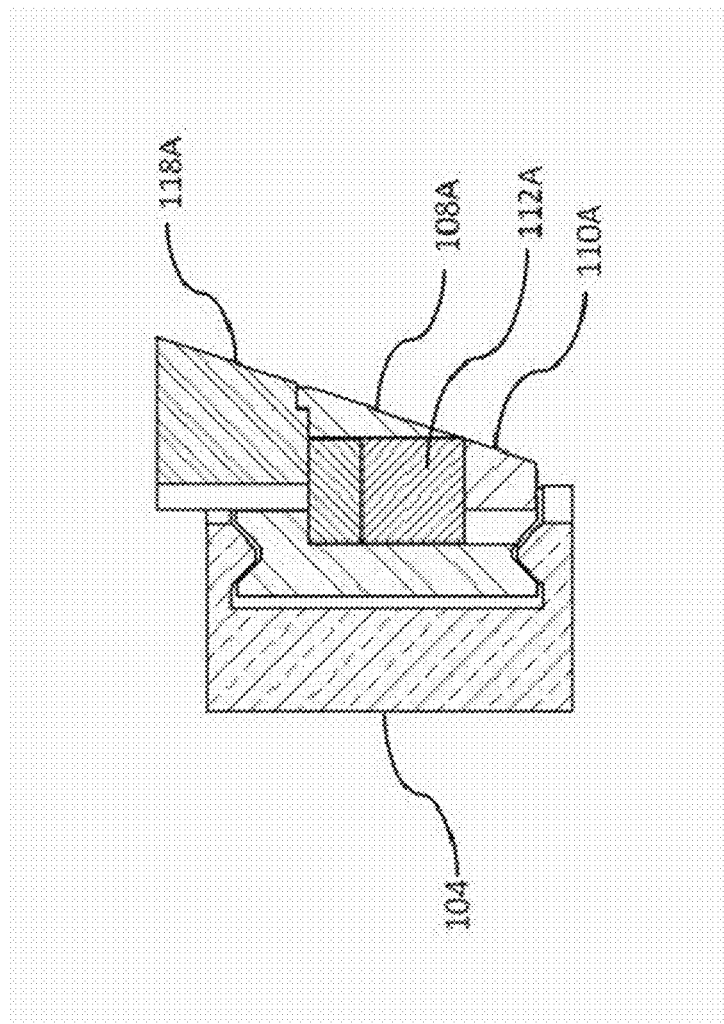
FIG. 5 shows a cross section view through the split ring assembly of FIG. 3 to illustrate an arrangement of magnets and spacer rings.

The split ring 106 is formed from two semi-circular components 108A and 108B, with each of the components formed of many layers. As shown in FIG. 3 and FIG. 4, the two semi-circular split ring halves, 108A and 108B, are connected to each other at a common end by means of a double hinge link 109 that allows the ring assembly to be opened to enable it to be installed around the item being inspected. The ends of the split ring halves, 108A and 108B, opposite the hinge include a latch 124B to secure the split ring ends together during the inspection process. A first one of the two split ring halves 108A includes a first-component top spacer 118A and a first-component bottom spacer 110A, each of the two spacer components possessing magnetic permeability. The terms "top" and "bottom" are used herein to distinguish the two first-component spacers 118A, 110A in relation to the orientation in FIG. 5. It should be understood that, in use, the so-called "top" spacer 118A will not always be oriented above the so-called "bottom" spacer 110A. As shown in FIG. 5, this first-component split ring half 108A incorporates openings suitable to locate and retain a plurality of first-component magnets 112A. First component split ring half 108A possesses magnetic reluctance. Furthermore, the first-component magnets 112A are installed such that their magnetic polarity is maintained with respect to the first-component top spacer 118A and first-component bottom spacer 110A. The magnets 112A are used to hold the split ring assembly onto the component being inspected. The arrangement of top spacer 118A and bottom spacer 110A with magnetic permeability, situated on either side of the magnetically reluctant split ring half 108A, increases the magnetic force holding the split ring 106 to the item being inspected.

The first-component magnets 112A, the first-component top spacer 118A and the first-component bottom spacer 110A are held together by a fastening means. As illustrated in FIG. 1, the fastening means may be, for example, a plurality of screws 120A, in which case, each of the first-component top spacer 118A and the first-component bottom spacer 110A define a plurality of apertures to accommodate the screws 120A. More particularly, the apertures (not shown) defined by the first-component bottom spacer 110A may be threaded to receive corresponding threads at the ends of the screws 120A.

The second one of the two semi-circular components includes a second assembly split ring half 108B, second component top spacer 118B, a second component bottom spacer 110B, screws 120B, and magnets 112B. The arrangement of the second semi-circular components is the same as the arrangement of the first set of semi-circular components.

The first-component split ring half 108A and second component split ring half 108B also define apertures 116 to accommodate pivot pins (not shown). The first one of the two split ring halves 108A may be attached to the double hinge link 109 which contains two apertures 116 by a pivot pin passing through the aperture 116 in the first-component split ring half 108A and the double hinge link 109, and the second split ring half 108B may also be attached to the double hinge link 109 by a pivot pin passing through the aperture 116 in the second-component split ring half 108B and the double hinge link 109.

To bias the first one of the two semi-circular components to form the split ring 106 with the second one of the two semi-circular components, a second-component, the latch 124B is provided.

The carriage 104 is formed to define a channel into which the split ring is slidably received and retained. FIG. 5 shows a cross section view of interface between the carriage 104 and split ring 106. To retain the split ring 106 in the channel, both the top and bottom walls of the channel in the carriage 104 define a protruding shape. The first-component split ring half 108A and the second-component split ring half 108B define top and bottom grooves with a profile corresponding to the protruding shape in the top and bottom walls of the channel in the carriage 104.

Figure 2:
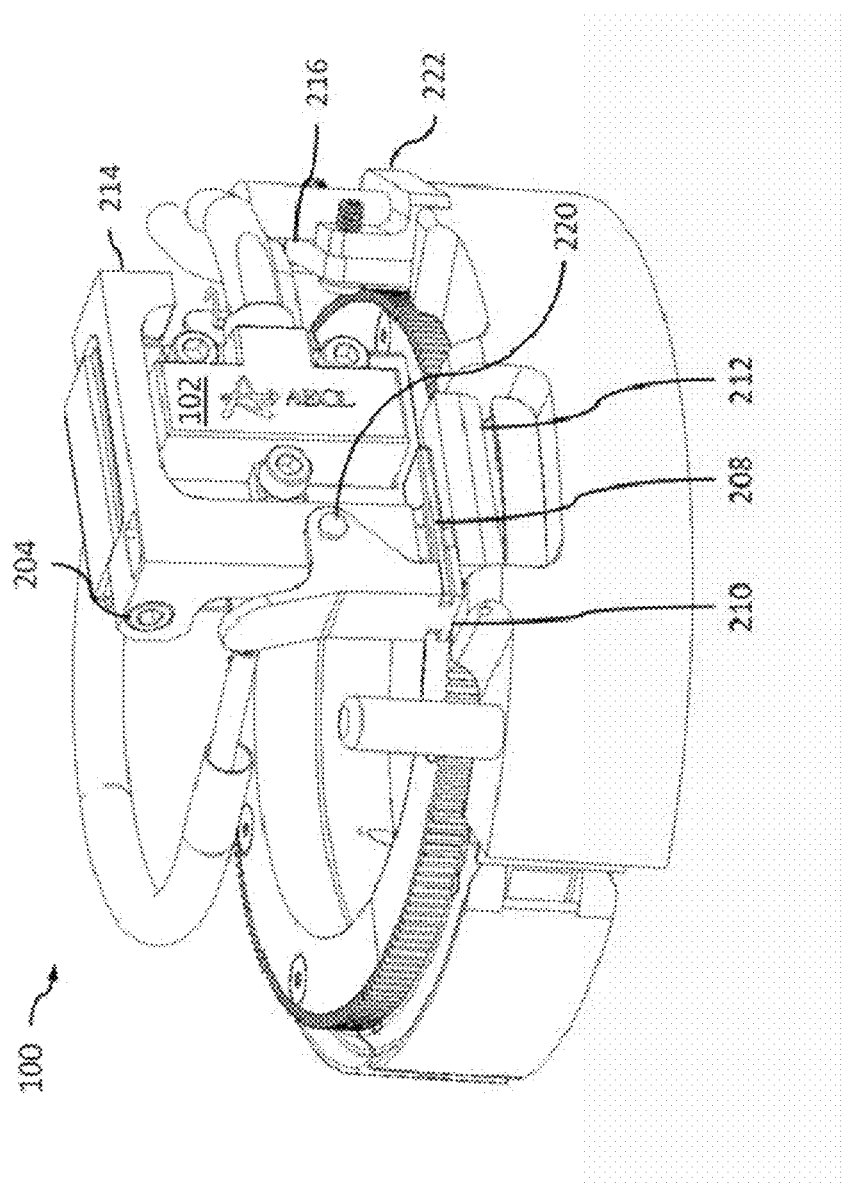
FIG. 2 illustrates a second view of the delivery tool assembly of FIG. 1.

The phased array ultrasonic probe 102 is mounted to a posterior side of a probe holder 126, which is pivotally mounted to the carriage 104 via a pivot arm 212 (see FIG. 2). As illustrated in FIG. 1, the probe holder 126 includes a pair of "wings", each wing defining at least one aperture. An aperture on each wing is arranged to accept each hooked end of a probe housing retainer spring 130. Mounted to an anterior side of the probe holder 126 is a transducer shoe 128 with a shape arranged to form to the component to be inspected. The transducer shoe 128 defines an aperture to allow a couplant to flow from the posterior side of the probe holder 126 to fill a cavity defined by the transducer shoe 128 and then to flow against the component to be inspected. A column of couplant formed in the cavity defined by the transducer shoe 128 enhances the operation of the phased array ultrasonic probe 102. De-mineralized water that remains in a container during approximately 24 hours prior to use is an example of couplant.

Figure 6:
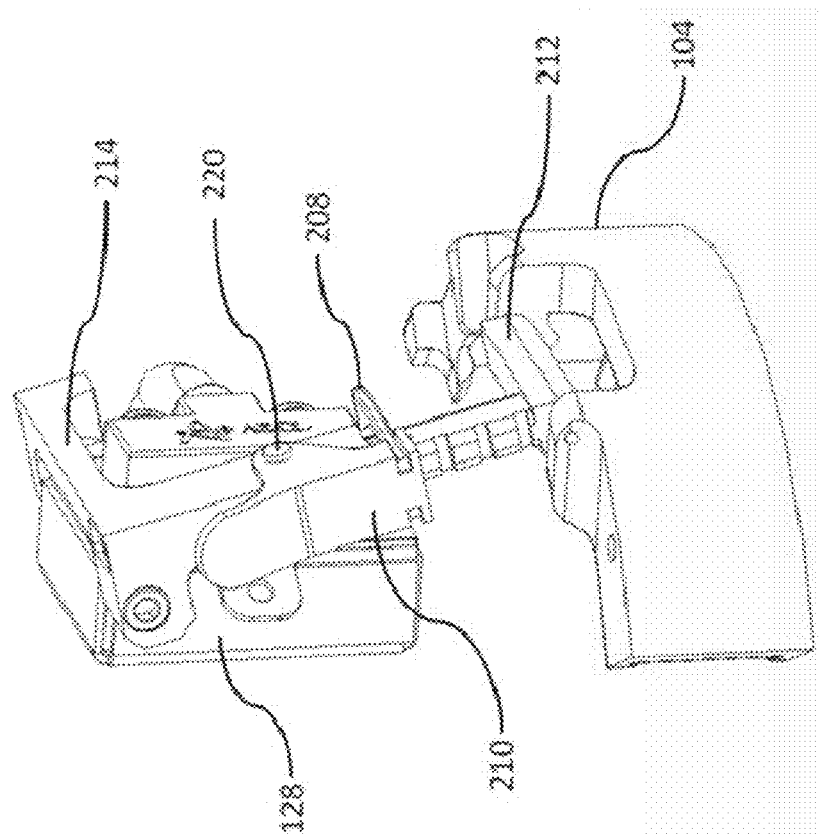
FIG. 6 shows a side view of a carriage, support arm and probe assembly portion of the delivery tool assembly of FIG. 1.

The means of attachment between the ultrasonic transducer shoe 128 and the carriage 104 is shown in FIG. 6. The pivot arm 212 is attached to the carriage 104 by the means of a pin (not shown) that allows rotation of the pivot arm 212 about an axis parallel to the top surface of the carriage 104 and tangent to the split ring. The pivot arm extension 214 is slidably received over the pivot arm 212. The shoe 128 is attached to the pivot arm extension 214 by a pin 204 that allows rotation of the shoe about an axis parallel to the top surface of the carriage 104 and tangent to the split ring. The pivot arm extension 214 is retained in relative position to the pivot arm 212 by means of a pivot arm latch 210. The pivot arm latch 210 is fixed by means of a pin 220 to the pivot arm extension 214. The pivot arm latch 210 engages in slots in the pivot arm 212 to set the relative position of the pivot arm extension 214 with respect to the pivot arm 212. The sliding action of the pivot arm extension 214 allows position of the ultrasonic probe 102 to be adjusted within the sliding motion of the components, enabling the ultrasonic probe 102 to be positioned to align it with a feature of interest on the component being inspected. The pinned connections from the carriage 104 to the pivot arm 212; and the pivot arm extension 214 to the shoe 128, allow the shoe 128 to adapt its position to follow the contour of the component being inspected.

Also mounted to the carriage 104 is a sensor bracket 222 and a non-contact sensor 216, which is fixed on the sensor bracket 222, FIG. 2. The non-contact sensor 216 is positioned to detect the gear teeth that are integral to the first-component top spacer 118A and the second-component top spacer 118B.

Together, the non-contact sensor 216, the first-component top spacer gear teeth 118A and the second-component top spacer gear teeth 118B serve to sense the rotary position of the carriage 104 with respect to the split ring 106. POSIC encoder ID1101G-00305-0508A09903, from POSIC SA of Neuchâtel, Switzerland, has been found to be suitable for use as the non-contact sensor 216.

Figure 7:
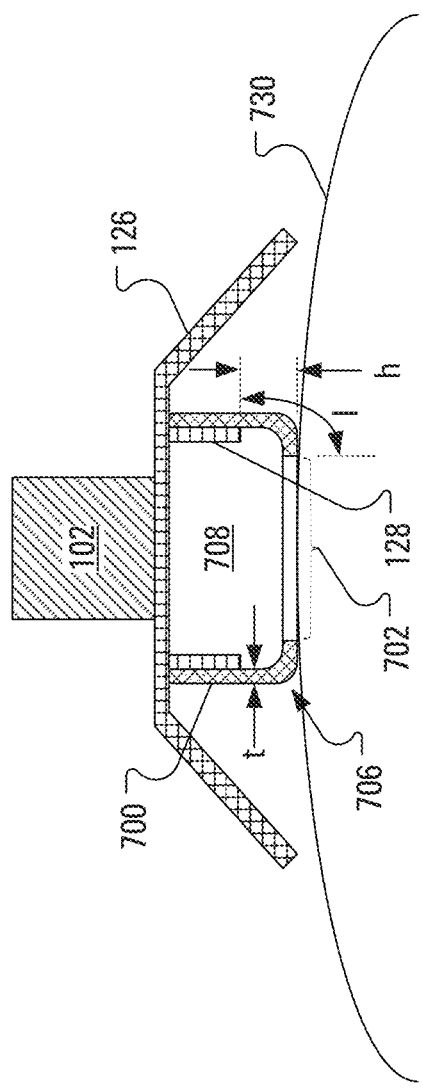
FIG. 7 illustrates, in a sectional view, an ultrasound-impermeable transducer shoe for use in the delivery tool assembly of FIG. 1.

FIG. 7 illustrates, in a sectional view, an ultrasound-impermeable transducer shoe membrane 700 defining an aperture 702. The ultrasound-impermeable transducer shoe membrane 700 of FIG. 7 is suitable for use with the transducer shoe 128 and helps to define a cavity 708 in which a column of couplant may be established. To facilitate attachment to the probe holder 126, the ultrasound-impermeable transducer shoe membrane 700 may be mounted to a rigid frame, which is transducer shoe 128. The transducer shoe 128 may also assist in defining the minimum height of the cavity and couplant column by providing, for example, contacting points with the surface 730 of a component to be examined. While aluminum is an example of a material suitable for forming the transducer shoe 128, fiber-reinforced neoprene is an example of a material suitable for forming the transducer shoe membrane 700. The transducer shoe membrane 700 may be fixed to the transducer shoe 128 by, for example, glue and/or screws (not shown). The transducer shoe 128 may be attached to the probe holder 126 by, for example, screws. If the transducer shoe is rectangular, which is only an example of a suitable shape, all four sides of the transducer shoe membrane 700 may be designed to include a bent edge 706. For reference, the transducer shoe membrane 700 is illustrated in FIG. 7 as being adjacent to a representative surface 730 of a component to be inspected.

The transducer shoe membrane 700 of FIG. 7 may be designed to meet the following criteria: water-tight seams; a low friction outside surface for contact with component to be inspected; flexibility suitable for following a complex topography and resistance to deformation. The resistance to deformation may be defined such that a lip of the bent edge 706, combined with the internal pressure of a column of couplant in the cavity 708, will exert a pressure against the surface 730 of the component to be inspected.

Figure 8:
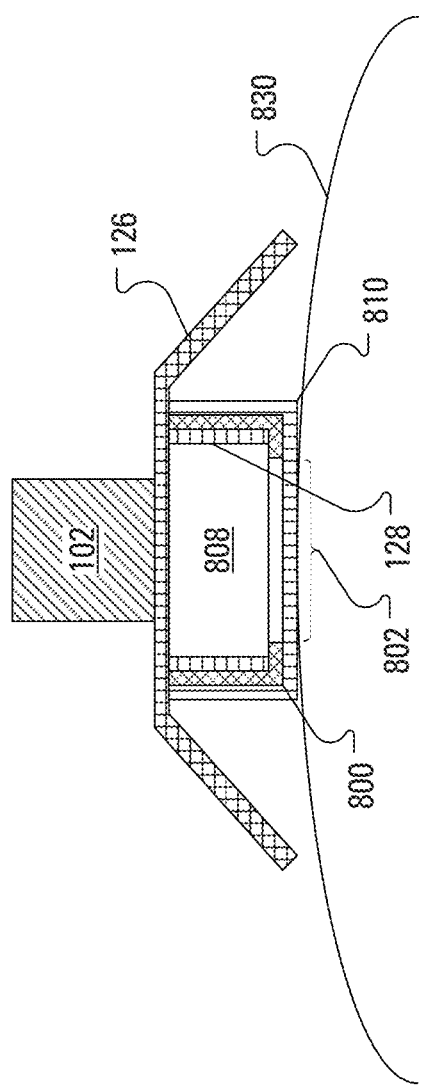
FIG. 8 illustrates, in a sectional view, an ultrasound-permeable transducer shoe for use in the delivery tool assembly of FIG. 1.

FIG. 8 illustrates an ultrasound-permeable transducer membrane 810, and an ultrasound-impermeable transducer membrane 800 defining an aperture 802. The ultrasound-permeable transducer shoe 810, together with the ultrasound-impermeable transducer membrane 800 and the rigid frame, which is transducer shoe 128 of FIG. 8, is suitable for use with the transducer shoe 128 and helps to define a cavity 808 in which a column of couplant may be established. To facilitate attachment to the probe holder 126, the ultrasound-impermeable transducer membrane 800 may be mounted to the transducer shoe 128. The ultrasound-permeable transducer membrane 810 may be mounted to the ultrasound-impermeable transducer membrane 800. An example of a material suitable for forming the transducer shoe membrane 800 is cotton canvas coated with silicon RTV-11. The transducer shoe membrane 800 may be fixed to the transducer shoe 128 by, for example, glue and/or screws (not shown). The transducer shoe 128 may be attached to the probe holder 126 by, for example, screws (not shown). For reference, the transducer shoe membrane 800 is illustrated in FIG. 8 as being adjacent to a representative surface 830 of a component to be inspected.

In contrast to the transducer shoe 700 of FIG. 7, the transducer shoe 800 of FIG. 8 is part of a closed membrane assembly. Indeed, an ultrasound-permeable transducer membrane 800 surrounds the transducer shoe 128 and is maintained in position by glue.

As mentioned, the transducer shoe membrane 800 may, for example, be formed of 100% cotton canvas coated with silicon RTV-11. The ultrasound-permeable transducer membrane 810 may, for example, be formed of nylon, with a urethane-coating on an inner surface (the surface against the transducer shoe membrane 800). The urethane may, for example, be abraded off during assembly to reduce attenuation of the ultrasonic signal produced by the phased array ultrasonic probe 102. In particular, the urethane may be removed, by abrasion, from the area of the membrane 810 that is exposed to the cavity 808 through the aperture 802.

The closed membrane assembly of FIG. 8, for which the transducer shoe membrane 800 is a part, may be designed to meet the following criteria: slightly permeable to water, with holes in the ultrasound-permeable transducer membrane 810 to allow couplant to come out and act as couplant between the membrane and the surface 830 of the component to be inspected; and flexible enough to conform to a complex topography.

The closed membrane assembly is a composite of the transducer shoe membrane 800 and the ultrasound-permeable transducer membrane 810 covering the aperture 802.

The transducer shoe membrane 800 allows the lighter ultrasound-permeable membrane 810 to conform to the complex topography of the inspection surface 830 of the component to be inspected.

When selecting a material for the ultrasound-impermeable transducer shoe membrane 700, many factors deserve consideration. Some factors relate to physical properties of the material used for the transducer shoe membrane. Such physical properties include thickness, resistance to bending (also referred to as "stiffness") and elasticity. Further factors relate to the form of the fold in the transducer shoe that permits the lip around the edge of the aperture 702 of the ultrasound-impermeable transducer shoe membrane 700 to seal against the inspection surface 730 of the component to be inspected.

For material of thickness "t" (see FIG. 7), a range of values may be quantified, and may be expressed in terms of "t", for a material extension with length "l" and height "h" of frame above the inspection surface 730.

Further factors influencing selection of a material for the transducer shoe membrane 700 involve design parameters that could influence the degree to which the centre of the transducer shoe 700 tents or puckers. The degree of tenting or puckering may, for example, dictate the height of a topographical feature, on the inspection surface 730, against which the transducer shoe membrane 700 can seal. Such design parameters may include the shape of the line of fold in the transducer shoe membrane 700 and can include reliefs or scallops.

To a distinct extent, the above factors also relate to the selection of a material for the transducer shoe membrane 800.

Figure 9:
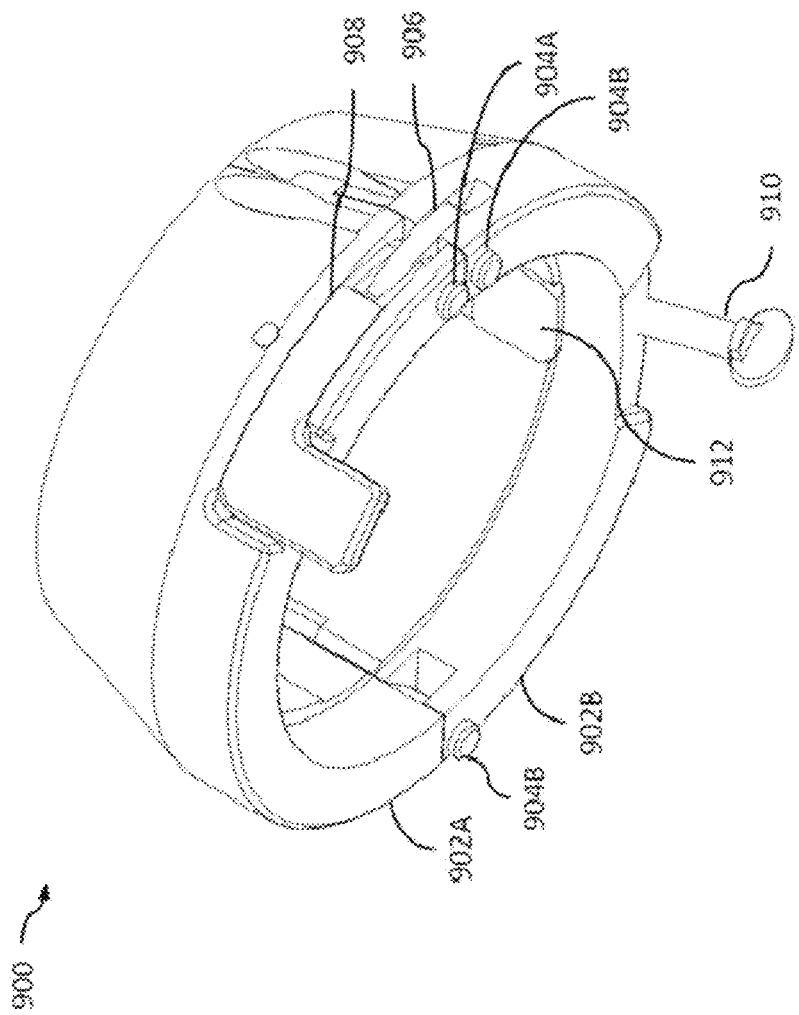
FIG. 9 illustrates an adapter assembly that allows installation of the delivery tool assembly of FIG. 1 on a straight pipe.

FIG. 9 illustrates an adaptor assembly 900 to install and use the delivery tool assembly 100, FIG. 1, on a straight pipe. The delivery tool assembly 100 is designed to be mounted onto a tapered surface, such as a Grayloc hub 1010 (see FIG. 10). Specifically, the profile of the top spacers 118A and 118 B and the bottom spacers 110A and 110B of the split ring 106 include a tapered surface to mate with the matching taper of a Grayloc hub 1010. It is desirable to have the flexibility to use the delivery tool assembly 100 to inspect sections of straight pipe. The adaptor assembly 900 is used to facilitate securing the delivery tool assembly onto a straight pipe section 1012.

The adaptor assembly 900 is circular in shape and is formed from two semi-circular components 902A and 902B. The two adaptor ring halves 902A and 902B are connected to each other at a common end by means of a pin 904B that passes through apertures in the semi-circular components 902A and 902B to form a hinged joint. This hinge allows the two halves of the adaptor assembly 900 to open up to allow the adaptor assembly 900 to be positioned around the pipe to be inspected. The opposite ends of the two semi-circular components 902A and 902B include a latch 908 to secure the adaptor ring ends together during the inspection process.

The inside diameter of the adaptor assembly 900 is designed to be slightly larger than the diameter of the pipe being inspected. The adaptor assembly 900 includes a clamping pad 912 that is mounted in an appropriate slot in the inside surface of the second-component adaptor ring half 902B. The clamping pad 912 can be extended inwards from the adaptor ring half 902B through the force applied by the clamp screw 910 that is mounted in a threaded aperture in adaptor ring half 902B. In use, the adaptor assembly 900 can be fixed to a straight pipe 1012 by turning the clamp screw 910 to extend the clamping pad 912 into firm contact with the pipe.

The adaptor assembly 900 has a tapered outer surface that practically matches the tapered profile of a Grayloc hub 1010. The delivery tool assembly 100 may be installed to interface onto the outer tapered surface of the adaptor assembly 900, in a manner similar to installation onto a Grayloc hub 1010. The delivery tool 100 is thereby secured onto the adaptor assembly 900, which is in turn secured onto the straight pipe section 1012. Inspection from the straight pipe section 1012 may therefore be performed by the delivery tool 100.

Ultrasonic phased arrays use a multiple element probe. An output pulse from each element in the probe is time delayed in such a way that a beam is generated. The beam produces constructive interference at a specific ultrasound angle and a specific depth. The time delay for the output pulse from each element can be incremented over a range of ultrasound angles to sweep the beam over a desired angular range.

In one wall thickness inspection technique, it is expected that an output pulse from a given element will result in a reflected signal from an outer wall surface (a first back-wall) and an inner wall surface (a second back-wall) of the component to be inspected. Receipt of each of the reflected pulses can be recorded and used to determine a time interval between the receipt of each of the reflected pulses.

Wall thickness may be calculated by measuring the time interval between receipt of the reflected pulses from the first back-wall and the second back-wall or the interface between the transducer shoe 128 and the component being inspected. A product may be formed from the time interval and the speed of sound in the material of the component. The product may then be divided by two. The speed of sound in the material is set at an average reference value, which is of 5927 m/sec for the components on which the inventors have tested the delivery tool assembly 100 of the present application.

The component to be inspected may be welded to a further component. As discussed above, erosion and corrosion are often found under and adjacent to welds due to flow accelerated corrosion. Accordingly, it may be the wall thickness at the weld that is of particular interest. Accordingly, the delivery tool assembly 100 of the present application may include a particularly uniquely design for the transducer shoe 128 that is mounted to the probe holder 126.

In preparation for use, three connections may be made to the delivery tool assembly 100 of FIG. 1. A first data connection (not shown) may be made between the phased array ultrasonic probe 102 and a control computer (not shown). As is typical, the control computer may include a processor, various types of short term and long term memory as well as various input and output interfaces. A second data connection (not shown) may be made between the non-contact sensor 216 and the control computer. A hydraulic connection (not shown) may also be made between the transducer shoe 128 and a supply of a liquid couplant.

Many main roles may be defined around an inspection: a Probe Operator operates the delivery tool assembly 100; an Ultrasonic Operator performs data acquisition and evaluates data acceptability; a Data Analyst analyses wall thickness data; a Resolution Analyst verifies all results produced by the Data Analysts; an Inspection Supervisor oversees the work of the Probe Operator and Ultrasonic Operator; and an Analysis Supervisor oversees the work of the Data Analysts and Resolution Analysts. Notably, one person can fulfill more than one role.

Initially, the Probe Operator installs either the delivery tool assembly 100 directly on the component to be inspected, if the delivery tool assembly 100 is not installed on a straight pipe 1012.

If the delivery tool assembly 100 is to be installed on a straight pipe 1012, the Probe Operator first installs the adaptor assembly 900 on the component to be inspected, then the Probe Operator installs the delivery tool assembly 100 on the adaptor assembly 900.

In particular, the Probe Operator may open the two semi-circular components of the split ring 106, with the two semi-circular components pivoting about the hinged link 122. To allow the two semi-circular components of the split ring 106 to open, the Probe Operator releases the second-component latch 124B.

Upon installing the delivery tool assembly 100 on the component to be inspected or the adapter assembly after installation on the component to be inspected, the Probe Operator acts to ensure the delivery tool assembly 100 will maintain its position on the component to be inspected, even when subject to various forces associated with use of the delivery tool assembly 100.

The Probe Operator may then check that the carriage 104 can slide on the split ring 106 with an acceptable amount of resistance. If unacceptable resistance is being felt, the Probe Operator may re-adjust the split ring 106 to ensure intimate contact of the inner faces of the top spacers 118A, 118B and the bottom spacers 110A, 110B with the component to be inspected.

The Probe Operator may then surround the component to be inspected with the probe housing retainer spring 130 and hook each end of the probe housing retainer spring 130 to a hole in respective wings of the probe holder 126.

The Ultrasonic Operator then establishes a computer setup file specifying a set of ultrasound angles and a scanning gain.

Programming or setting up the phased array ultrasonic probe 102 should aim to produce a number of linear scans of the elements. The number of elements per focal law (excitation pattern), resolution (meaning element increment), emission focus position of each focal law and pulser voltage should be optimized to produce the best possible combination of the reflected pulses from the first back-wall and the second back-wall of the component being inspected.

If the first back-wall and the second back-wall are suspected to be non-parallel, then refracted angles should be used to produce the best possible combination of reflected pulses on the component being inspected.

Figure 10:
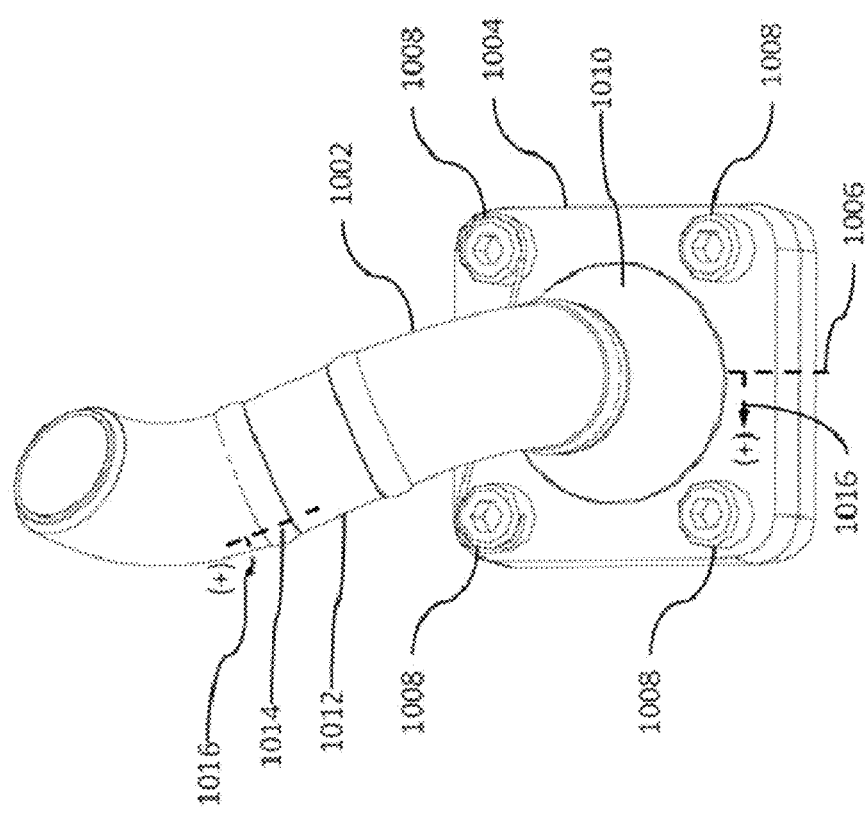
FIG. 10 illustrates, in an isometric view, a component to be inspected by the delivery tool assembly of FIG. 1.

FIG. 10 illustrates an isometric view of a component to be inspected 1002 assembled to a flange 1004. The component to be inspected includes a tapered Grayloc hub 1010 that is welded to join the component to be inspected 1002 and the flange 1004. The flange 1004 is fastened to a further structure by set of bolts 1008. A zero circumferential position 1006 may be defined as between the two front bolts 1008 or at the center of the right cheek of an arc 1014. The right cheek of an arc 1014 may be determined based on the Probe Operator facing a face of the further structure (e.g., reactor) to which the flange 1004 is bolted. Additionally, reference numeral 1016 is assigned to the clockwise direction around the component to be inspected 1002, to be referred to as the "positive" direction.

In situations in which the component to be inspected 1002 defines an arc, the Probe Operator may then move the phased array ultrasonic probe 102 circumferentially to the intrados of the arc. The Probe Operator may then move the phased array ultrasonic probe 102 axially to cover the breadth of the weld of interest.

The Ultrasonic Operator then starts a pump when the Probe Operator is ready. The pump controls the flow of couplant to the probe holder 126.

The Probe Operator may then move the phased array ultrasonic probe 102 back and forth circumferentially to remove air bubbles from the couplant inside the transducer shoe cavity 708 and 808.

The Ultrasonic Operator may then check data quality. Such a check may confirm, for example, that no air bubbles are detected by the phased array ultrasonic probe 102, that the column of couplant is maintained and that the breadth of the weld is covered.

Upon confirming that the data quality is sufficient, the Probe Operator may, responsive to instructions from the Ultrasonic Operator, move the phased array ultrasonic probe 102 to the zero circumferential position 1006 or 1014.

Upon receiving confirmation that the phased array ultrasonic probe 102 has been moved to the zero circumferential position 1006 or 1014, the Ultrasonic Operator may set the non-contact sensor 216 to zero.

The Probe Operator may then, responsive to instructions from the instrument operator, move the phased array ultrasonic probe 102 to a negative position equivalent to approximately −45°.

Upon receiving confirmation that the phased array ultrasonic probe 102 has been moved to the negative position equivalent to approximately −45°, the Ultrasonic Operator may initiate data collection for a positive scan. Such initiation may involve use of a data collection program executed on the control computer. The Ultrasonic Operator may interact with a user interface of the data collection program to initiate data collection.

Upon receiving confirmation that the Ultrasonic Operator has initiated the positive scan, the Probe Operator circumferentially moves the carriage 104 carrying the phased array ultrasonic probe 102 in the positive direction 1016. Caution should be exercised by the Probe Operator to protect the cables from getting tangled, caught or damaged as the Probe Operator moves the carriage 104 past the zero circumferential position 1006 or 1014 and stops the carriage 104 when the phased array ultrasonic probe 102 is centered at a positive position equivalent to approximately +45°. While the carriage is moved by the Probe Operator, the non-contact sensor 216 transfers circumferential position readings, which are representative of position of the phased array ultrasonic probe 102 on the component to be inspected, from the non-contact sensor 216 to the control computer (not shown) for encoding.

The ultrasonic inspection involves a total of four dimensions. The first dimension is time and each ultrasonic signal is voltage versus time (A-scan). The second dimension is axial position and there is a plurality of ultrasonic signals (A-scans), one for each axial position; this is called a D-scan. The third dimension is circumferential position and there is a D-scan for each circumferential position. Wall Thickness is calculated at each of the (axial, circumferential) co-ordinates to form a two-dimensional Wall Thickness map. The fourth dimension is ultrasound angle. There is a three dimensional data set for each ultrasound angle that could in principle form a two-dimensional Wall Thickness map for each ultrasound angle. However, in the end only one two-dimensional composite Wall Thickness map is produced by the data analyst from all of the ultrasound angles. The data collection program executed on the control computer associates each sample, where a sample is a D-scan, for each ultrasound angle, reported by the phased array ultrasonic probe 102 on a position along the scan path.

Responsive to the arrival of the phased array ultrasonic probe 102 at +45°, the Ultrasonic Operator may terminate data collection. Such termination may involve use of a data collection program executed on the control computer. The Ultrasonic Operator may interact with the user interface of the data collection program to terminate data collection.

The Ultrasonic Operator may then check the data quality. One aspect of the data quality that the Ultrasonic Operator may check involves checking that the full circumference of the component is inspected, checking for indications of a loss of interface signal and checking that the entire weld is covered by the inspection. Notably, loss of interface signal may only be permitted at the edges of the weld cap due to the high localized curvature. Another aspect of the data quality that the Ultrasonic Operator may check involves checking that no air bubbles caused a loss of back-walls. A further aspect of the data quality that the Ultrasonic Operator may check involves checking that the Probe Operator did not scan too quickly. Evidence of scanning too quickly includes presence of white strips of missing data. Such white strips could prevent a valid data analysis from being performed. An additional aspect of the data quality that the Ultrasonic Operator may check involves checking that there is no obvious problem with the non-contact sensor 216. For example evidence there is no obvious problem with the non-contact sensor 216, the Ultrasonic Operator may confirm that the position recorded at the end of the scan corresponds to a realistic value fairly close to +45°.

Data acquired during a scan operation using the delivery tool assembly 100 may be analyzed to obtain wall thickness information. More particularly, data points acquired during the scan operation include position information (non-contact sensor 216 information) and signal information regarding reflected signals received at the phased array ultrasonic probe 102. The signal information may be converted from time-domain information to frequency-domain samples using the known Discrete Fourier Transform.

Obtaining wall thickness information from the data acquired during the scan operation may require some interpolation of the frequency-domain samples.

The Applicants reviewed many interpolation methods in detail as to their suitability to the present application. One method, which uses just three points from the A-scan, is specified in Jacobsen, P. Kootsookos, "Fast, Accurate Frequency Estimators", IEEE Signal Processing Magazine, pages 123-125, May 2007 (hereinafter "Jacobsen", the entirety of which is incorporated herein by reference). Jacobsen proposes estimating $\hat{x}_p$, a position of a peak, from $$\hat{x}_p = x_p + T_\delta \left( \frac{y_{p+1} - y_{p-1}}{4y_p - 2(y_{p+1} + y_{p-1})} \right) \qquad (1)$$

where p is the index of the peak sample in the raw (not interpolated) sequence;
$x_p$ is the position of the sample at index p;
$y_i$ is the sequence amplitude at index i; and
$T_\delta$ is the sampling interval.

This interpolation method may be shown to provide interpolation to within 1.3 μm (1 sample standard deviation).

Figure 11:
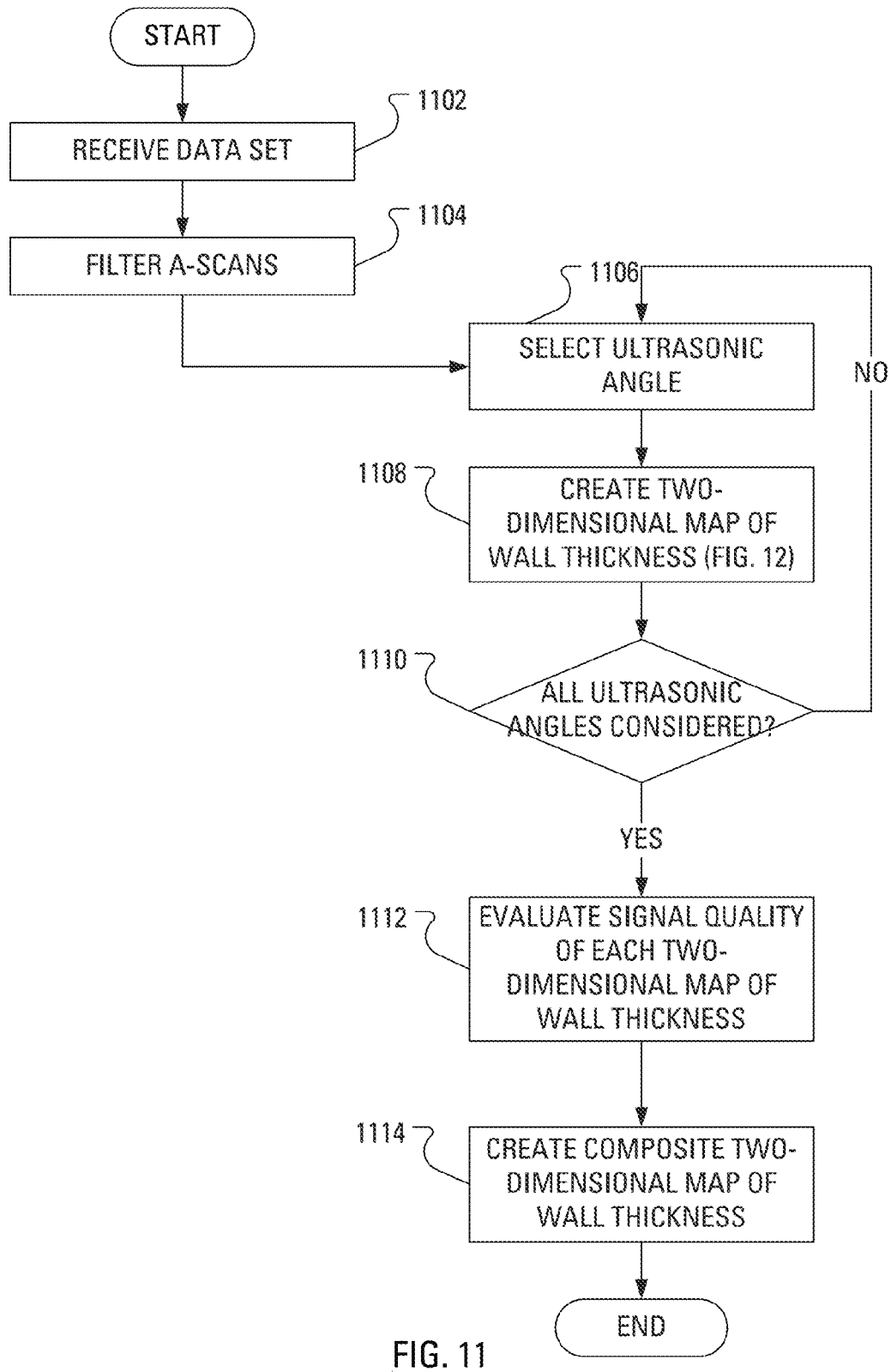
FIG. 11 illustrates steps in a method of creating a plurality of two-dimensional maps of Wall Thicknesses.

Creation of a Wall Thickness map begins with receipt of a data set acquired during a scan operation. As described above, the data set may be characterized as having a voltage associated with each of four dimensions: time; axial position; circumferential position; and ultrasonic angle. The final output is a single Wall Thickness map with a Wall Thickness calculated at each circumferential and axial location from the multiple ultrasound angles in the data set. FIG. 11 illustrates steps in a method of creating a plurality of two-dimensional maps of Wall Thicknesses. The method may be carried out on a general purpose computer including a processor and memory to store instructions for execution by the processor.

Initially, the processor receives (step 1102) the data set. The processor then filters (step 1104) the ultrasonic A-scans to remove noise. The processor then selects an ultrasonic angle (step 1106) and creates (step 1108) a two-dimensional wall thickness map to associate with the selected ultrasonic angle.

Figure 12:
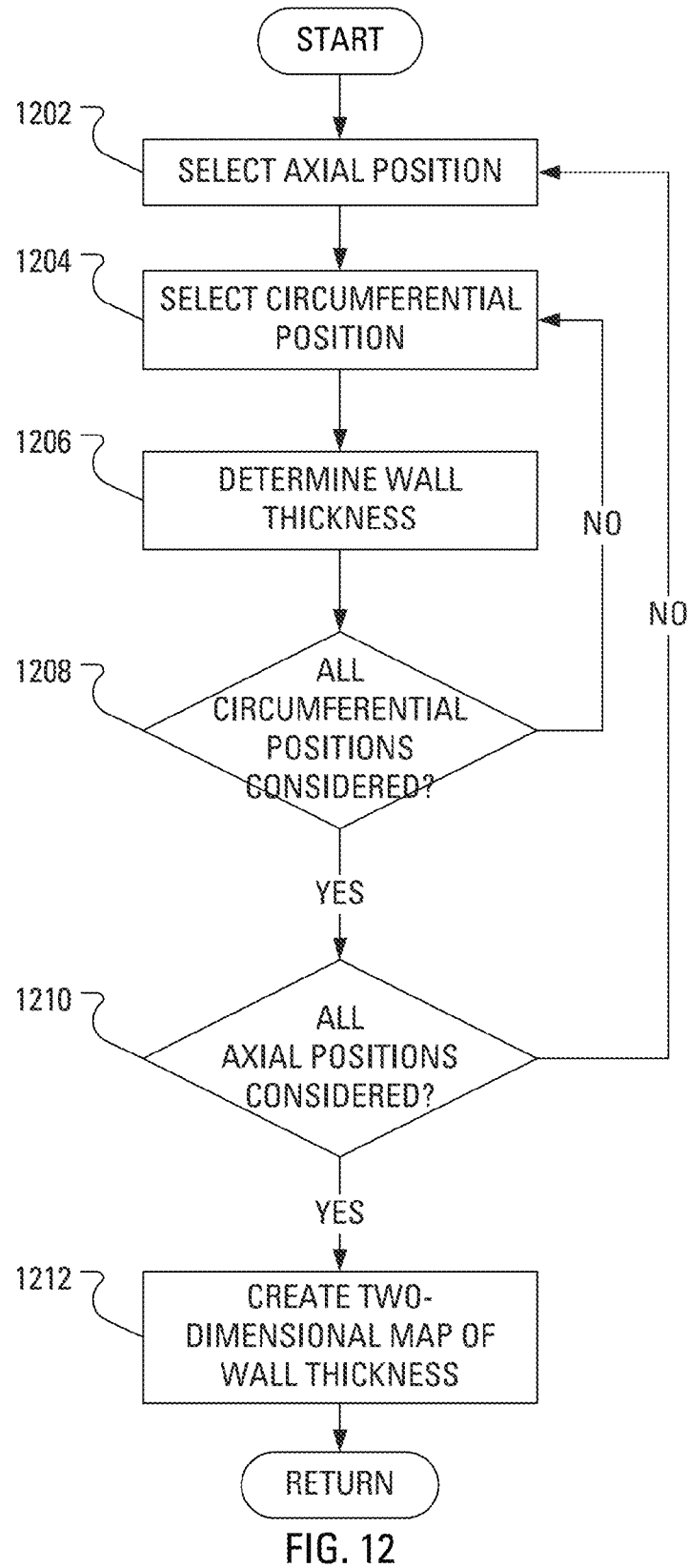
FIG. 12 illustrates steps in a method of creating one of the two-dimensional Wall Thickness maps as part of the method illustrated in FIG. 11.

Detail of creation (step 1108) of the two-dimensional Wall Thickness map are presented in FIG. 12. Initially, the processor selects (step 1202) an axial position. The processor subsequently selects (step 1204) a circumferential position. The processor then determines (step 1206) a wall thickness.

With the ultrasonic angle, axial position and circumferential position fixed, the data may be considered to be a set of voltage samples, with each voltage sample associated with a time. Accordingly, the wall thickness determining (step 1206) may employ equation (1) to locate, by interpolation, the position of a first peak and a second peak. The time-interval between the first and second peaks may be expressed as a Wall Thickness value associated with the selected axial position and the selected circumferential position.

Upon departing the phased array ultrasonic probe 102, an ultrasonic signal passes through the couplant and reaches a front surface of the component being inspected. A first portion of ultrasonic signal reflects off the front surface and returns to the phased array ultrasonic probe 102 as a front surface echo, where the front surface echo is detected. A second portion of the ultrasonic signal refracts through the front surface and proceeds through the thickness of the wall to the other surface of the wall of the component being inspected, "the other surface" may be called a "back wall". While some of the second portion of the ultrasonic signal passes through the back wall, a first back-wall echo of the second portion of the ultrasonic signal proceeds back in the direction of the front surface. Some of the first back-wall echo passes through the front surface and is detected by the phased array ultrasonic probe 102. Some of the first back-wall echo passes reflects off the front surface in the direction of the back wall and creates a second back-wall echo. Some of the second back-wall echo passes through the front surface and is detected by the phased array ultrasonic probe 102.

In one mode of the wall thickness determining (step 1206), the first peak is representative of the first back-wall echo and the second peak is representative of the second back-wall echo. In another mode of the wall thickness determining (step 1206), the first peak is representative of the front surface echo and the second peak is representative of the first back-wall echo.

The processor then determines (step 1208) whether all circumferential positions have been considered. Upon determining (step 1208) that all circumferential positions have not been considered, the processor selects (step 1204) a further circumferential position.

Upon determining (step 1208) that all circumferential positions have been considered, the processor then determines (step 1210) whether all axial positions have been considered. Upon determining (step 1210) that all axial positions have not been considered, the processor selects (step 1202) a further axial position.

Upon determining (step 1210) that all axial positions have not been considered, the processor creates (step 1212) a two-dimensional map of Wall Thicknesses for the selected ultrasound angle. The map includes a Wall Thickness value for each coordinate pair comprising a circumferential position and an axial position.

Upon determining (step 1210) that all axial positions have been considered, the processor may then determine (step 1110, FIG. 11) whether all ultrasonic angles have been considered. Upon determining (step 1110) that all ultrasonic angles have not been considered, the processor selects (step 1106) a further ultrasonic angle. Upon determining (step 1110) that all ultrasonic angles have been considered, the processor may evaluate (step 1110) the signal quality of each A-scan corresponding to each position in each two-dimensional map of Wall Thicknesses to reject un-reliable thickness estimates, by comparing the following items to software selectable values: signal-to-noise ratio, minimum signal amplitude, frequency content, minimum amplitude of auto correlations, minimum amplitude of cross correlations, and the minimum ratio of second peak correlation amplitudes to that of the first peak.

Following the automated calculation of Wall Thickness maps for each ultrasound angle, the qualified operator may then create (step 1114) a single, final wall thickness map based upon operator interpretation of the data. The operator may, for example, employ software tools to straighten an interface signal to facilitate wall thickness calculation. The operator may also employ software tools to select a particular ultrasound angle and analysis mode (see step 1206, FIG. 12) for a specific region of the map. Additionally, the operator may manually evaluate signal quality in the specific region to reject low-quality wall thickness estimates. The operator may then paint the specific region on the final wall thickness map. The operator may repeat these previous steps for all other regions of the map to create final wall thickness map.

The above-described implementations of the present application are intended to be examples only. Alterations, modifications and variations may be effected to the particular implementations by those skilled in the art without departing from the scope of the application, which is defined by the claims appended hereto.

What is claimed is:

1. An apparatus for inspecting a component, the apparatus comprising:
 a magnetized split ring to maintain a position on said component;
 a carriage mounted on said split ring in a manner allowing said carriage to rotate around said split ring;
 a transducer shoe, connected to said carriage by a pivoting arm, with said transducer shoe maintaining, by a first flexible, ultrasound-impermeable membrane, a cavity for receiving a couplant, said first flexible, ultrasound-impermeable membrane also defining an aperture;
 a phased array ultrasonic probe, mounted to said transducer shoe, said probe adapted to emit, through said couplant and through said aperture, a plurality of ultrasonic output pulses from each element of a plurality of elements, said plurality of output pulses emitted at a plurality of incidence angles;
 a second membrane surrounding said first membrane, said second membrane permeable to couplant and to said ultrasonic output pulses; and
 an encoder adapted to provide angular position information.

2. The apparatus of claim 1 wherein said first flexible membrane comprises fiber-reinforced neoprene.

3. The apparatus of claim 1 wherein said probe is adapted to:
 acquire a data point representative of a reflection of each output pulse of said plurality of output pulses.

4. The apparatus of claim 3 wherein said first membrane comprises cotton canvas coated with silicon RTV-11.

5. The apparatus of claim 1 further comprising an adaptor assembly configured to adapt the apparatus to a straight pipe.

* * * * *